United States Patent [19]

Paget et al.

[11] 4,082,762

[45] Apr. 4, 1978

[54] 4-(2-HALOPHENYL)-1,2,4-TRIAZOLE-3-THIOL COMPOUNDS

[75] Inventors: Charles J. Paget, Indianapolis; James H. Wikel, Greenwood, both of Ind.

[73] Assignee: Eli Lilly and Company, Indianapolis, Ind.

[21] Appl. No.: 739,158

[22] Filed: Nov. 5, 1976

Related U.S. Application Data

[62] Division of Ser. No. 607,848, Aug. 25, 1975, Pat. No. 4,008,242, which is a division of Ser. No. 449,141, Mar. 7, 1974, Pat. No. 3,937,713.

[51] Int. Cl.$^2$ ............................................. C07D 249/12
[52] U.S. Cl. ............................... 260/308 R; 260/308 C
[58] Field of Search ........................ 260/308 C, 308 R

[56] References Cited

U.S. PATENT DOCUMENTS

| | | | |
|---|---|---|---|
| 3,067,250 | 12/1962 | Oja | 260/552 SC |
| 3,594,390 | 7/1971 | Timmler et al. | 260/308 C |
| 3,799,759 | 3/1974 | Martin et al. | 260/552 SC |
| 3,867,395 | 2/1975 | Seidel et al. | 260/308 C |

FOREIGN PATENT DOCUMENTS

| | | | |
|---|---|---|---|
| 1,273,881 | 9/1961 | France | 260/308 C |
| 1,549,674 | 12/1967 | France | 260/308 R |
| 1,049,054 | 11/1966 | United Kingdom | 260/308 R |
| 1,066,215 | 4/1967 | United Kingdom | 260/308 R |

OTHER PUBLICATIONS

Cole et al., Chem. Abstracts, vol. 66, Abstract No. 110059w (1967).
Fuji II, Chem. Abstracts, vol. 67, Abstract No. 38283r (1967).
Shah et al. I, J. Sci. Ind. Res., vol. 21C, pp. 76–78 (1962).
Shah et al. II, Chem. Abstracts, vol. 57, col. 16601e (1962).
Postovskii et al., Chem. Abstracts, vol. 63, col. 13242b–13243d, (1965).
Shegal et al., Khim. Geterotsikl. Soedin., Akad. Nauk Latv., SSR, 1965, pp. 443–448.
Bhat et al. I, Chem. Abstracts, vol. 68, Abstract No. 59501w (1968).
Bhat et al. II, Indian J. Chem., vol. 5, pp. 397–401 (1967).
Pesson II, Chem. Abstracts, vol. 57, col. 9860f (1962).
Wikel et al., J. Org. Chem., vol. 39, pp. 3506–3508 (1974).

*Primary Examiner*—Alton D. Rollins
*Attorney, Agent, or Firm*—Kathleen R. S. Page; William B. Scanlon; Everet F. Smith

[57] ABSTRACT

A novel process for the preparation of s-triazolo-[3,4-b]benzothiazole compounds comprises reacting a molar equivalent of base in an amide solvent at a temperature from 60° C. to 200° C. with (a) a 1-acyl-4-(o-halophenyl)thiosemicarbazide compound or (b) a 4-(o-halophenyl)-1,2,4-triazole-3-thiol compound and recovering the product. The s-triazolo [3,4-b]benzothiazole compounds are useful for the control of plant pathogens.

7 Claims, No Drawings

4-(2-HALOPHENYL)-1,2,4-TRIAZOLE-3-THIOL COMPOUNDS

This is a division of application Ser. No. 607,848 filed Aug. 25, 1975 and issued Feb. 15, 1977 as U.S. Pat. No. 4,008,242. Application Ser. No. 607,848 is in turn a division of application Ser. No. 449,141 filed Mar. 7, 1974 and issued Feb. 10, 1976, as U.S. Pat. No. 3,937,713.

BACKGROUND OF THE INVENTION

Certain substituted s-triazolo [3,4-b]benzothiazoles (hereinafter referred to as "triazolobenzothiazole compounds") are employed for the control of plant pathogens, including fungal organisms and bacterial organisms. Thus, the triazolobenzothiazole compounds can be employed for the control of such organisms as crown gall, rice blast, leaf rust, powdery mildew, anthracnose, and the like. The compounds are particularly suited for the control of fungal organisms, and give particularly good results in the control of rice blast. Belgium Pat. No. 789,918 describes their preparation by cyclodehydration of 2-acylhydrazinobenzothiazole compounds with polyphosphoric acid.

It is a purpose of this invention to provide a novel process for the preparation of triazolobenzothiazole compounds, useful as plant fungicides, and in addition to provide new intermediate 1-acyl-4-(o-halophenyl)thiosemicarbazide compounds and 4-(o-halophenyl)-1,2,4-triazole-3-thiol compounds which are utilized in the preparation of such triazolobenzothiazole compounds.

SUMMARY OF THE INVENTION

This invention relates to a novel process for the preparation of s-triazolo [3,4-b]benzothiazole compounds represented by the formula

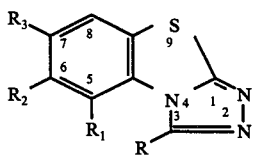

which comprises commingling at least a molar equivalent of base in a substantially anhydrous amide solvent at a temperature from about 60° C. to about 200° C. with (a) an equimolar mixture of an acylhydrazine of the formula

and an o-halophenylisothiocyanate of the formula

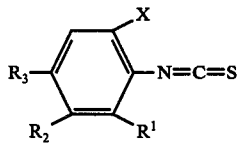

which has been maintained a temperature of about 60° C. to about 100° C. for about 24 hours; or (b) a 1-acyl-4-(o-halophenyl)thiosemicarbazide of the formula

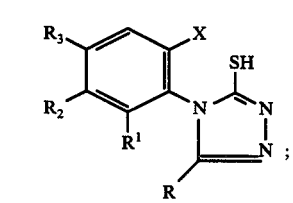

or (c) a 4-(o-halophenyl)-1,2,4-triazole-3-thiol of the formula

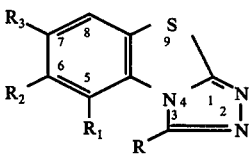

and recovering the product;
wherein, in the foregoing formulae, R is hydrogen, $C_1$-$C_{11}$ alkyl, cyclopropyl or trifluoromethyl; $R_1$ is hydrogen, bromo, chloro or fluoro; $R_2$ and $R_3$ are independently hydrogen, $C_1$-$C_3$ alkyl, $C_1$-$C_3$ alkoxy, bromo, chloro, fluoro or trifluoromethyl with the limitation that at least one of $R_2$ and $R_3$ is hydrogen; X is bromo, chloro or fluoro; and subject to the further limitations that when $R_1$ is halogen, R is other than hydrogen and $R_2$ is hydrogen.

In addition this invention is concerned with the preparation of the novel intermediate 1-acyl-4-(o-halophenyl)-3-thiosemicarbazide and the 4-(o-halophenyl)-1,2,4-triazole-3-thiol compounds which are used to prepare the triazolobenzothiazole plant fungicides.

DETAILED DESCRIPTION OF THE INVENTION

This invention relates to a novel process for the preparation of s-triazolo [3,4-b]benzothiazole compounds represented by the formula

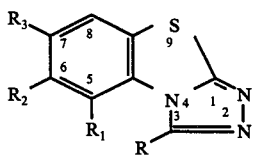

wherein
R is hydrogen, $C_1$-$C_{11}$ alkyl, cyclopropyl or trifluoromethyl;
$R_1$ is hydrogen, bromo, chloro or fluoro;
$R_2$ and $R_3$ are independently hydrogen; $C_1$-$C_3$ alkyl, $C_1$-$C_3$ alkoxy, bromo, chloro, fluoro or trifluoromethyl with the limitation that at least one of $R_2$ and $R_3$ is hydrogen;
subject to the further limitations that when $R_1$ is halogen, R is other than hydrogen and $R_2$ is hydrogen;
which comprises commingling a molar equivalent of base in a substantially anhydrous amide solvent at a temperature from about 60° C. to about 200° C. with
  a. a 1-acyl-4-(o-halophenyl)-3-thiosemicarbazide compound; or
  b. a 4-(o-halophenyl)-1,2,4-triazole-3-thiol compound; and recovering the product.

The term "$C_1$-$C_{11}$ alkyl" represents branched or straight-chain alkyl groups of from 1 to 11 carbon atoms. Exemplary of such straight-chain alkyl groups are methyl, propyl, pentyl, hexyl, octyl, decyl, and the like. Exemplary of the branched chain alkyl groups are isopropyl, t-butyl, isopentyl, neopentyl, isohexyl, 3-methylpentyl, 2,3,5-trimethylhexyl, 2,5-dimethyl-4-ethylheptane and the like. The term "$C_1$-$C_3$ alkyl" includes methyl, ethyl, propyl and isopropyl. The term "$C_1$-$C_3$ alkoxy" represents ether groups such as methoxy, ethoxy, propoxy, and isopropoxy. Where the term "halo" or "halogen" is employed, it refers to bromine, chlorine and fluorine only.

In addition, this invention is concerned with the preparation of the useful intermediate 1-acyl-4-(o-halophenyl)-3-thiosemicarbazide compounds, represented by the formula

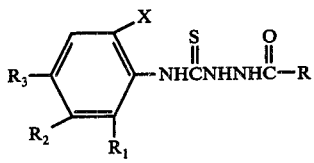

II and the 4-(o-halophenyl)-5-substituted-1,2,4-triazole-3-thiol compounds, represented by the formula

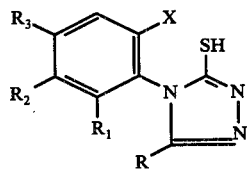

III wherein R, $R_1$, $R_2$, $R_3$ and X are as defined hereinabove. These novel intermediate compounds are utilized in the process of the present invention by reaction with a molar equivalent of base in a substantially anhydrous amide solvent.

All the starting materials and intermediates required in the instant process are prepared by methods known to the art. The 1-acylhydrazine compounds represented by the formula

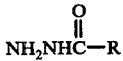

are prepared by reacting hydrazine with the appropriate acid derivatives such as the acid chloride, the anhydride or the ester. [see Organic Reactions, Vol. 3, N.Y., Wiley, 1946, pp. 366–369].

The o-halophenylisothiocyanate compounds represented by the formula

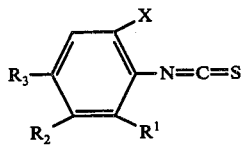

are prepared by reacting the appropriate o-haloanilines with dimethylaminothiocarbamoyl chloride in an aromatic solvent [see J. Org. Chem., 30, 2465 (1965)].

The intermediate 1-acyl-4-(o-halophenyl)-3-thiosemicarbazide compounds, are prepared by reacting the aforementioned starting materials in an aprotic solvent at elevated temperatures. The thiosemicarbazides in turn are converted to the triazolothiol compounds by reaction with aqueous base, as described in Ind. J. Chem., 5 (9), 397 (1967); Chem. Abst. 68, 59501w (1968). The reaction sequence leading to the triazolothiol compounds is outlined below.

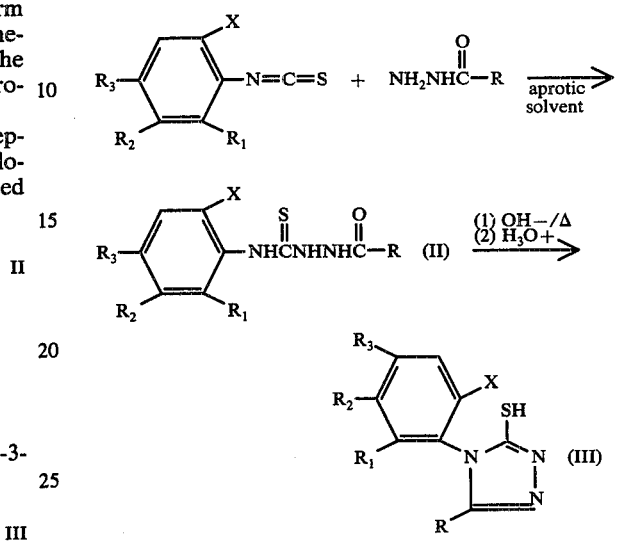

After initial thiosemicarbazide formation a double intramolecular cyclization is effected to produce the benzothiazole: (1) a cyclodehydration to provide the triazolothiol and (2) an aromatic halogen displacement to provide the desired benzothiazole compound. The cyclodehydration provides a 4-(o-halophenyl) -1,2,4-triazole-3-thiol which undergoes aromatic halogen displacement by thiol anion generated in the presence of base to provide the instant triazolobenzothiazole compound.

In the halogen displacement reaction by thiol anion, $R_1$ is equivalent to X when both are bromo, chloro or fluoro. One of $R_1$ or X is displaced to provide a 5-bromo, 5-chloro- or 5-fluorotriazolobenzothiazole. When $R_1$ and X are separately bromo, chloro or fluoro, mixtures of 5-chloro-, 5-bromo- and 5-fluoro-triazolobenzothiazoles are obtained. Such mixtures are separable by methods such as fractional crystallization or chromatography. The process operates when $R_1$ or X is iodo; however, the required o-iodophenylisothiocyanate starting materials are less readily available. They are more difficult to prepare and render the process less economical.

In general, it appears that electronegative phenyl substituents facilitate halogen displacement as evidenced by high product yields and short reaction times. Electron donating substituents such as methyl tend to retard halogen displacement resulting in increased reaction times and production of dimeric side products.

The 1-acyl-4-(o-halophenyl) -3-thiosemicarbazide compounds are prepared by reacting molar equivalents of an acylhydrazine compound and an o-halophenylisothiocyanate in a substantially anhydrous aprotic solvent at a temperature from about 60° C. to about 100° C for about 24 hours. A substantially anhydrous aprotic solvent refers to a type of solvent which does not offer or accept protons but which might possibly still contain trace amounts of water. Exemplary of the aprotic solvents employed are benzene, dichloroethane, dioxane, the dimethylether of ethylene glycol, tetrahydrofuran (THF), and the like. THF is a preferred solvent for the preparation of the thiosemicarbazide compounds. The thiosemicarbazide product is recovered by evaporation of the solvent and purified by conventiona methods.

The 4-(o-halophenyl)-5-substituted-1,2,4-triazole-3-thiol compounds are prepared from the corresponding thiosemicarbazide compounds by cyclodehydration with a molar equivalent of an alkali metal hydroxide in an aqueous or dilute $C_1$-$C_3$ carbinol medium. Exemplary of suitable carbinol solvents are methanol, ethanol, propanol and isopropanol. The preferred cyclodehydration conditions are aqueous sodium hydroxide and steam bath temperature. If desired, the triazolothiol salt can be obtained by evaporation of the solvent and heated in an amide solvent to provide the triazolobenzothiazole compounds. Usually, however, the basic mixture is acidified and the insoluble triazolothiol compound is recovered for use in the process.

It will be noted that it is not necessary to isolate the intermediate thiosemicarbazides or triazolothiols to operate the process.

Solvents which may be employed in the instant process are commonly used tertiary amide solvents, which are unreactive with the starting materials and product. A substantially anhydrous tertiary amide solvent can be used. The term "substantially anhydrous" means that the presence of small amounts of water can be tolerated in the solvent. Generally the amide solvent can be "dried" in situ by using one to ten percent excess of base to react with the residual water. Exemplary of the amide solvents which are employed are N,N-dibutylacetamide, dimethylacetamide (DMAC), dimethylformamide (DMF), N-methyl-2-pyrrolidone, and the like. The higher amide solvents are effective because of their higher boiling temperatures. For reasons of availability and ease of removal, DMAC and DMF are preferred solvents.

In general, any base which is strong enough to generate a triazolothiol anion is suitably employed in the instant process. Although a molar equivalent of base is sufficient, the base serves a dual function. It participates (1) in triazolothiol formation and (2) in the intramolecular displacement of halogen by thiol anion. In addition to the lithium alkyls such as methyl lithium and butyl lithium, suitable bases include the alkoxides, amides, carbonates, hydrides and hydroxides of the alkali metals. Among these are lithium ethoxide, potassium t-butoxide, sodium methylate and the like. The carbonates and hydroxides of lithium, sodium, potassium, cesium and rubidium can be used. The preferred bases which can be employed in the process of this invention are lithium amide, sodium amide, potassium amide, sodium hydride, potassium hydride and the like.

The instant process is operated at a temperature range from about 60° C. to about 200° C. When the process is operated with the acylhydrazine and isothiocyanate compounds, an induction period at a temperature of about 60° C. to about 100° C. for about 24 hours is employed to generate the 1-acyl-4-(o-halophenyl)-3-thiosemicarbazide intermediate in situ. After the induction period, a molar equivalent of the preferred sodium hydride is added and the reaction is completed at a temperature of about 160° C, the boiling temperature of the preferred DMF solvent. When the thiosemicarbazide or triazolothiol compound is employed in the process, it is dissolved in the DMF, a molar equivalent of the preferred sodium hydride is added and the reaction mixture is brought to reflux temperature for a period of time sufficient to complete the reaction. Generally, the process is completed within 24 hours or less at a temperature between 60° C. and 100° C. Halogen displacement by thiol anion is influenced by the nature of the phenyl substituent groups. When $R_2$ and $R_3$ are electron donating groups such as $C_1$-$C_3$ alkyl, halogen displacement is retarded, thereby requiring extended reaction times.

All the triazolobenzothiazole compounds provided by this invention are useful for the control of plant pathogens, particularly rice blast.

Illustrative of the 1-acyl-4-(o-halophenyl)-3-thiosemicarbazide compounds which can be employed in the process of this invention are the following:

4-(2-chlorophenyl)-1-formyl-3-thiosemicarbazide
1-acetyl-4-(2-chlorophenyl)-3-thiosemicarbazide
1-acetyl-4-(2-chloro-5-methylphenyl)-3-thiosemicarbazide
1-acetyl-4-(2-chloro-5-trifluoromethylphenyl)-3-thiosemicarbazide
1-acetyl-4-(2-chloro-4-methylphenyl)-3-thiosemicarbazide
1-acetyl-4-(2,5-dichlorophenyl)-3-thiosemicarbazide
4-(2-chlorophenyl)-1-heptanoyl-3-thiosemicarbazide
1-acetyl-4-(2-chloro-5-methoxyphenyl)-3-thiosemicarbazide
1-butyryl-4-(2-chloro-5-trifluoromethylphenyl)-3-thiosemicarbazide
4-(2-chlorophenyl)-1-cyclopropanecarbonyl-3-thiosemicarbazide
1-cyclopropanecarbonyl-4-(2,6-dichlorophenyl)-3-thiosemicarbazide
4-(2-chlorophenyl)-1-trifluoroacetyl-3-thiosemicarbazide
4-(2,6-dichloro-4-propoxyphenyl-1-trifluoroacetyl-3-thiosemicarbazide
4-(2-chloro-5-ethoxyphenyl)-1-propionyl-3-thiosemicarbazide
4-(2-bromo-6-fluoro-5-methylphenyl)-1-valeryl-3-thiosemicarbazide
1-isobutyryl-4-(2,4,6-trichlorophenyl)-3-thiosemicarbazide
4-(2-chloro-6-fluorophenyl)-1-decanoyl-3-thiosemicarbazide
4-(2-bromo-6-fluoro-5-methoxyphenyl)-1-butyryl-3-thiosemicarbazide
4-(2,6-dichloro-4-trifluorophenyl)-1-trifluoroacetyl-3-thiosemicarbazide
4-(2-chloro-6-fluoro-5-trifluoromethyl)-1-cyclopropanecarbonyl-3-thiosemicarbazide.

Illustrative of the 4-(o-halophenyl)-5-substituted-1,2,4-triazole-3-thiol compounds which can be employed in the process of this invention are the following:

4-(2-chlorophenyl)-1,2,4-triazole-3-thiol
4-(2-chlorophenyl)-5-methyl-1,2,4-triazole-3-thiol
4-(2-chloro-5-trifluoromethylphenyl)-5-methyl-1,2,4-triazole-3-thiol
4-(2,4-dichlorophenyl)-5-methyl-1,2,4-triazole-3-thiol
4-(2-chloro-4-methylphenyl)-5-methyl-1,2,4-triazole-3-thiol
4-(2,6-dichlorophenyl)-5-methyl-1,2,4-triazole-3-thiol
4-(2-chloro-5-methylphenyl)-5-methyl-1,2,4-triazole-3-thiol
4-(2-chloro-5-methoxyphenyl)-5-methyl-1,2,4-triazole-3-thiol 5-propyl-4-(2-chloro-5-trifluoromethylphenyl)-1,2,4-triazole-3-thiol
4-(2-chlorophenyl)-5-cyclopropyl-1,2,4-triazole-3-thiol
5-cyclopropyl-4-(2,6-dichlorophenyl)-1,2,4-triazole-3-thiol
4-(2-chlorophenyl-5-trifluoromethyl-1,2,4-triazole-3-thiol
4-(2,6-dichloro-4-propoxyphenyl)-5-trifluoromethyl-1,2,4-triazole-3-thiol
4-(2-chloro-5-ethoxyphenyl)-5-ethyl-1,2,4-triazole-3-thiol
4-(2-bromo-6-fluoro-5-methylphenyl)-5-butyl-1,2,4-triazole-3-thiol
5-isopropyl-4-(2,4,6-trichlorophenyl)-1,2,4-triazole-3-thiol
4-(2-chloro-6-fluorophenyl)-5-monyl-1,2,4-triazole-3-thiol
4-(2-bromo-6-fluoro-5-methoxyphenyl)-5-propyl-1,2,4-triazole-3-thiol
4-(2,6-dichloro-4-fluoro-5-trifluoromethylphenyl)-5-trifluoromethyl-1,2,4-triazole-3-thiol
4-(2-chloro-6-fluoro-5-trifluoromethylphenyl)-5-cyclopropyl-1,2,4-triazole-3-thiol Illustrative of the triazolobenzothiazole compounds provided by this invention are the following:
s-triazolo(3,4-b)benzothiazole
3-methyl-s-triazolo(3,4-b)benzothiazole
7-chloro-3-methyl-s-triazolo(3,4-b)benzothiazole
5-chloro-3-methyl-s-triazolo(3,4-b)benzothiazole
3,7-dimethyl-s-triazole(3,4-b)benzothiazole
3-heptyl-s-triazolo(3,4-b)benzothiazole
3-methyl-5-trifluoromethyl-s-triazolo(3,4-b)benzothiazole
3,6-dimethyl-s-triazolo(3,4-b)benzothiazole
6-methoxy-3-methyl-s-triazolo(3,4-b)benzothiazole
3-propyl-6-trifluoromethyl-s-triazolo(3,4-b)benzothiazole
3-cyclopropyl-s-triazolo(3,4-b)benzothiazole
5-chloro-3-cyclopropyl-s-triazolo(3,4-b)benzothiazole
3-trifluoromethyl-s-triazolo(3,4-b)benzothiazole
5-chloro-7-propoxy-3-trifluoromethyl-s-triazolo(3,4-b)benzothiazole
3-ethyl-6-ethoxy-s-triazolo(3,4-b)benzothiazole
5-fluoro-6-methyl-3-butyl-s-triazolo(3,4-b)benzothiazole
5,7-dichloro-3-isopropyl-s-triazolo(3,4-b)benzothiazole
5-fluoro-3-nonyl-s-triazolo(3,4-b)benzothiazole
5-fluoro-6-methoxy-3-propyl-s-triazolo(3,4-b)benzothiazole
5-chloro-3,7-bis(trifluoromethyl)-s-triazolo(3,4-b)benzothiazole
3-cyclopropyl-5-fluoro-6-trifluoromethyl-s-triazolobenzothiazole The following examples further illustrate the preparation of the starting materials, intermediates and compounds of our invention.

(I) PREPARATION OF THIOSEMICARBAZIDES

EXAMPLE 1

Preparation of
1-formyl-4-(2-fluorophenyl)-3-thiosemicarbazide

Fifty grams (0.33 mole) of 2-fluorophenylisothiocyanate and 20 g. (0.33 mole) of formylhydrazine were refluxed for 7 hours in 500 ml. of tetrahydrofuran (THF). The reaction mixture was allowed to cool and the insoluble product was collected by filtration. The crude product was washed with water, filtered and dried. The yield was 10 g. of 1-formyl-4-(2-fluorophenyl)-3-thiosemicarbazide, mp. about 148°–149° C.

Analysis: $C_8H_8FN_3OS$: MW 213: Calc: C, 45.06; H, 3.78; N, 19.71. Found: C, 44.86; H, 3.55; N, 19.44.

EXAMPLE 2

Preparation of
1-acetyl-4-(2-chloro-5-methylphenyl)-3-thiosemicarbazide

One tenth mole, 18.3 g., of 2-chloro-5-methylphenylisothiocyanate and 11.0 g. (0.15 mole) of acetylhydrazine were refluxed for 7 hours in 500 ml. of THF. After cooling, the insoluble product was collected by filtration. The crude product was collected by filtration. The crude product was washed with water, filtered and dried. The yield was 25 g. of 1-acetyl-4-(2-chloro-5-methylphenyl)-3-thiosemicarbazide, m.p. about 145°–157° C.

Analysis: $C_{16}H_{12}ClN_3OS$: MW 257: Calc: C, 46.60; H, 4.69; N, 16.30. Found: C, 46.87; H, 4.92; N, 16.58.

EXAMPLES 3–7

The following 1-acetyl-4-substituted (o-halophenyl)-3-thiosemicarbazides were prepared from acetylhydrazine and the appropriate o-halophenylisothiocyanates by the method of Example 2

1-acetyl-4-(2-chlorophenyl)-3-thiosemicarbazide, m.p. about 152°–153° C.

Analysis: $C_9H_{10}ClN_3OS$:NW 243: Calc: C, 44.35; H, 4.14; N, 17.24. Found: C, 46.23; H, 4.28; N, 17.64.

1-acetyl-4-(2-chloro-4-methylphenyl)-3-thiosemicarbazide, m.p. about 157°–159° C.

Analysis: $C_{10}H_{12}ClN_3SO$: MW 257: Calc: C, 46.60; H, 4.69; N, 16.30. Found: C, 46.37; H, 4.67; N, 16.50.

1-acetyl-4-(2,4-dichlorophenyl)-3-thiosemicarbazide, m.p. about 145°–147° C.

Analysis: $C_9H_9Cl_2N_3SO$: MW 278: Calc: C, 38.86; H, 3.26; N, 15.11. Found: C, 39.02; H, 3.39; N, 15.02.

1-acetyl-4-(2,6-dichlorophenyl)-3-thiosemicarbazide, m.p. about 157°–159° C.

Analysis: $C_9H_9Cl_2N_3SO.H_2O$:MW 296: Calc: C, 36.48; H, 3.71; N, 14.19. Found: C, 36.49; H, 3.84; N, 14.67.

1-acetyl-4-(2-chloro-5-trifluoromethylphenyl)-thiosemicarbazide, m.p. about 155°–156° C.

Analysis: $C_{10}H_9ClF_3N_3SO$: MW 311: Calc: C, 38.53; H, 2.91; N, 13.48. Found: C, 38.86; H, 3.21; N, 13.83.

(II) PREPARATION OF TRIAZOLES

EXAMPLE 8

Preparation of 4-(2-fluorophenyl)-1,2,4-triazole-3-thiol

One and one-tenth grams (20 mmoles) of potassium hydroxide were dissolved in 50 ml. of water. 1-Formyl-4-(2-fluorophenyl)thiosemicarbazide, 3.5 g. (16.5 mmoles), was dissolved in the basic solution by warming on the steam bath until solution was completed. The heating was continued for one hour. The cooled reaction mixture was poured into a dilute solution of hydrochloric acid. The insoluble product was recovered from the acidic solution by filtration. The product was washed with water, collected and dried. The yield was 2.5 g. of 4-(2-fluorophenyl)-1,2,4-triazole-3-thiol, m.p. about 166°–167° C.

Analysis: $C_8H_6FN_3S$: MW 196: Calc: C, 49.22; H, 3.10; N, 21.53. Found: C, 49.09; H, 3.13; N, 21.37.

EXAMPLES 9-17

The following 4-(2-halophenyl)-1,2,4-triazole-3-thiols were prepared from the appropriately substituted thiosemicarbazides by cyclization in aqueous or alcoholic base by the method of Example 8:

4-(2-chlorophenyl)-1,2,4-triazole-3-thiol, m.p. about 195°-196° C.

Analysis: $C_8H_6ClN_3S$: MW 211.5: Calc: C, 45.39; H, 2.96; N, 19.85. Found C, 45.48; H, 3.10; N, 19.70.

4-(2-chlorophenyl)-5-methyl-1,2,4-triazole-3-thiol, m.p. about 217°-219° C.

Analysis: $C_9H_8ClN_3S$: MW 225: Calc: C, 47.89; H, 3.57; N, 18.62. Found: C, 47.73; H, 3.64; N, 18.39.

4-(2,4-dichlorophenyl)-5-methyl-1,2,4-triazole-3-thiol, m.p. about 248°-253° C.

Analysis: $C_9H_9Cl_2N_3S$: MW 260: Calc: C, 41.55; H, 2.71; N, 16.15. Found: C, 41.57; H, 2.81; N, 16.37.

4-(2-chloro-4-methylphenyl)-5-methyl-1,2,4-triazole-3-thiol, m.p. about 243°-244° C.

Analysis: $C_{10}H_{10}ClN_3S$: MW 239: Calc: C, 50.10; H, 4.20; N, 17.53. Found: C, 50.23; H, 4.24; N, 17.73.

4-(2-chloro-5-methylphenyl)-5-methyl-1,2,4-triazole-3-thiol, m.p. about 229°-231° C.

Analysis: $C_{10}H_{10}ClN_3S$: MW 239: Calc: C, 50.10; H, 4.20; N, 17.53. Found: C, 49.89; H, 4.27; N, 17.40.

4-(2,6-dichlorophenyl)-5-methyl-1,2,4-triazole-3-thiol, m.p. about 240°-242° C.

Analysis: $C_9H_7Cl_2N_3S$: NW 260: Calc: C, 41;55; H, 2.71; N, 16.15. Found: C, 41.32; H, 2.80; N, 15.98.

4-(2-chloro-6-methylphenyl)-1,2,4-triazole-3-thiol, m.p. about 237°-240° C.

Analysis: $C_9H_8ClN_3$: MW 225: Calc: C, 48.00; H, 3.55; N, 18.66. Found: C, 48.00; H, 3.32; N, 18.62.

4-(2-chloro-5-trifluoromethylphenyl)-5-methyl-1,2,4-triazole-3-thiol, m.p. about 208°-209° C.

Analysis: $C_{10}H_7ClF_3NS$: MW 293: Calc: C, 40.90; H, 2.40; N, 14.31. Found: C, 40.95; H, 2.42; N, 14.27.

4-(2-chlorophenyl)-5-heptyl-1,2,4-triazole-3-thiol, m.p. about 150°-157° C.

Analysis: $C_{15}H_{20}ClN_3S$: MW 309: Calc: C, 58.14; H, 6.51; N, 13.56. Found: C, 57.95; H, 6.33; N, 13.79.

(III) PREPARATION OF TRIAZOLOBENZOTHIAZOLES

EXAMPLE 18

Preparation of s-triazolo [3,4-b]benzothiazole

Five grams (30.0 mmoles) of o-chlorophenylisothiocyanate were dissolved in 50 ml. of dry DMF. A solution of 1.8 g. (30.0 mmoles) of formylhydrazine in 50 ml. of dry DMF was added dropwise rapidly to the stirred reaction mixture. The temperature of the reaction rose to about 45° C. The temperature was maintained between 60° C. and 100° C. for 24 hours. Thirty millimoles, 1.5 g., of sodium hydride as a 50% mineral oil suspension was added to the reaction mixture. The reaction was completed by heating at reflux temperature (160° C) for about 185 hours. The cooled mixture was poured into water. The aqueous mixture was extracted with n-hexane to remove mineral oil. The product was extracted with ethyl acetate. The ethyl acetate extract was washed (water), dried (MgSO$_4$) and evaporated in vacuo to a residual oil. the oil was covered with dry ether an the product crystallized upon standing. The yield of s-triazolo[3,4-b]benzothiazole, m.p. about 175°-176° C., was 200 mg.

Analysis $C_8H_5N_3S$: MW 175: Calc: C, 54.85; H, 2.88; N, 23.98. Found: C, 54.56; H, 2.94; N, 23.79.

EXAMPLE 19

Preparation of 3-methyl-s-triazolo(3,4-b)benzothiazole

Ten millimoles, 2.4 g., of 1-acetyl-4-(2-chlorophenyl)-thiosemicarbazide where dissolved in 50 ml. of dimethylformamide (DMF) under nitrogen. One equivalent, 0.5 g. (10 mmoles), of sodium hydride, as a 50% mineral oil dispersion, was added to the reaction mixture. After refluxing for 126 hours, the reaction mixture was poured into water. The aqueous mixture was extracted with hexane to remove mineral oil followed by extraction with chloroform. The chloroform extract was dried (MgSO$_4$) and evaporated in vacuo to yield 400 mg. of 3-methyl-s-triazolo(3,4-b)-benzothiazole.

Analysis: $C_9H_7N_3S$: MW 189: Calc: C, 57.12; H, 3.73; N, 22.21. Found: C, 56.84; H, 3.79; N, 22.23.

EXAMPLE 20

Preparation of 7-chloro-3-methyl-s-triazolo[3,4-b]-benzothiazole

Five grams (19 mmoles) of 4-(2,4-dichlorophenyl)-5-methyl-1,2,4-triazole-3-thiol were dissolved in 100 ml. of DMF. One gram (20 mmoles) of sodium hydride, as a 50% mineral oil dispersion, was added portionwise to the stirred reaction mixture. The mixture was refluxed for 24 hours and then poured into 600 ml. of water. The aqueous mixture was extracted with n-hexane to remove the mineral oil. The aqueous phase was extracted with ethyl acetate overnight by means of a liquid-liquid extractor. The ethyl acetate was dried (MgSO$_4$) and evaporated in vacuo to a residue. The residue was washed with toluene and the crystalline product was collected by filtration. The yield was 1.9 g. of 7-chloro3-methyl-s-triazolo[3,4-b]benzothiazole, m.p. about 186°-188° C. a second crop, 1.6 g., m.p, about 185°-188° C., was recovered from the aqueous phase.

Analysis: $C_9H_6ClN_3S$: MW 224: Calc: C, 48.33; H, 2.70; N, 18.79. Found: C, 48.32; H, 2.89; N, 18.96.

We claim:

1. A 4-(o-halophenyl)-1,2,4-triazole-3-thiol compound of the formula

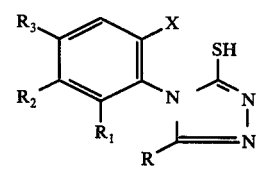

wherein
R is hydrogen, $C_1$-$C_{11}$ alkyl, cyclopropyl or trifluoromethyl;
$R_1$ is hydrogen, bromo, chloro or fluoro;
$R_2$ and $R_3$ are independently hydrogen, $C_1$-$C_3$ alkyl, $C_1$-$C_3$ alkoxy, bromo, chloro, fluoro or trifluoromethyl with the limitation that at least one of $R_2$ and $R_3$ is hydrogen;
X is bromo, chloro or fluoro;
subject to the further limitation that when $R_1$ is halogen, R is other than hydrogen and $R_2$ is hydrogen.

2. The compound of claim 1 which is 4-(2-chlorophenyl)-1,2,4-triazole- b 3-thiol.

3. The compound of claim 1 which is 4-(2-chlorophenyl)-5-methyl-1,2,4-triazole-3-thiol.

4. The compound of claim 1 which is 4-(2,4-dichlorophenyl)-5-methyl-1,2,4-triazole-3-thiol.

5. The compound of claim 1 which is 4-(2,6-dichlorophenyl)-5-methyl-1,2,4-triazole-3-thiol.

6. The compound of claim 1 which is 4-(2-chloro-5-methylphenyl)-5-methyl-1,2,4-triazole-3-thiol.

7. The compound of claim 1 which is 4-(2-chloro-5-trifluoromethylphenyl)-1,2,4-triazole-3-thiol.

* * * * *

UNITED STATES PATENT AND TRADEMARK OFFICE
CERTIFICATE OF CORRECTION

PATENT NO. : 4,082,762
DATED : April 4, 1978
INVENTOR(S) : Charles J. Paget et al.

It is certified that error appears in the above-identified patent and that said Letters Patent are hereby corrected as shown below:

Column 9, line 66, "an" should read --and--.

Claim 2, line 66, "-1,2,4-triazole- b 3-thiol" should read -- -1,2,4-triazole-3-thiol --.

Signed and Sealed this

Eighth Day of May 1979

[SEAL]

Attest:

RUTH C. MASON
Attesting Officer

DONALD W. BANNER
Commissioner of Patents and Trademarks